(12) United States Patent
Ferguson et al.

(10) Patent No.: US 7,107,857 B2
(45) Date of Patent: *Sep. 19, 2006

(54) APPARATUS FOR AN ANVIL SYSTEM THAT PROVIDES ENHANCED SELF-RESISTIVE SPECIMEN HEATING WHEN USED IN A DYNAMIC THERMO-MECHANICAL MATERIAL TESTING SYSTEM

(75) Inventors: David E. Ferguson, Averill Park, NY (US); Norman A. Lindeman, Sand Lake, NY (US)

(73) Assignee: Dynamic Systems Inc., Poestenkill, NY (US)

( * ) Notice: Subject to any disclaimer, the term of this patent is extended or adjusted under 35 U.S.C. 154(b) by 43 days.

This patent is subject to a terminal disclaimer.

(21) Appl. No.: 10/877,662

(22) Filed: Jun. 25, 2004

(65) Prior Publication Data

US 2005/0011275 A1 Jan. 20, 2005

Related U.S. Application Data

(60) Provisional application No. 60/482,623, filed on Jun. 26, 2003.

(51) Int. Cl.
*G01N 3/08* (2006.01)
(52) U.S. Cl. .................................................. 73/818
(58) Field of Classification Search ................ 73/818
See application file for complete search history.

(56) References Cited

U.S. PATENT DOCUMENTS

| | | | |
|---|---|---|---|
| 2,375,033 A * | 5/1945 | Parke et al. .................. 374/46 |
| 3,012,126 A | 12/1961 | Ferguson ...................... 219/20 |
| 3,854,030 A * | 12/1974 | Roye ............................ 219/72 |
| 3,994,158 A * | 11/1976 | Weinhold ..................... 73/798 |
| 5,092,179 A * | 3/1992 | Ferguson ..................... 73/790 |
| 5,195,378 A | 3/1993 | Ferguson ..................... 73/790 |
| 5,659,140 A * | 8/1997 | Jakob et al. .................. 73/788 |
| 5,959,215 A * | 9/1999 | Ono et al. .................... 73/798 |
| 6,422,090 B1 * | 7/2002 | Ferguson ..................... 73/795 |
| 6,742,440 B1 * | 6/2004 | Ferguson et al. ............ 92/13.1 |

OTHER PUBLICATIONS

U.S. Appl. No. 10/877,655, filed Jun. 25, 2004.

* cited by examiner

*Primary Examiner*—Edward Lefkowitz
*Assistant Examiner*—George P Bonanto
(74) *Attorney, Agent, or Firm*—Michaelson & Associates; Peter L. Michaelson

(57) ABSTRACT

Apparatus for use in a conventional dynamic material testing system to advantageously provide uniform self-resistive specimen heating with enhanced temperature uniformity. Specifically, an anvil stack (300) in an anvil assembly (200) has a foil interface (242) with a composite layer (320$_A$, 320$_B$, 320$_C$) containing, e.g., a concentrically oriented multi-component arrangement formed of an inner high strength and insulating disk (315, 325, 335) and an outer ring-shaped resistive region (313, 323, 333), situated between an anvil base (241) and an anvil top (240). An insulating member (243) electrically and thermally insulates all sides of the anvil stack from its supporting structure.

25 Claims, 3 Drawing Sheets

APPARATUS FOR AN ANVIL SYSTEM THAT PROVIDES ENHANCED SELF-RESISTIVE SPECIMEN HEATING WHEN USED IN A DYNAMIC THERMO-MECHANICAL MATERIAL TESTING SYSTEM

CLAIM TO PRIORITY

This application claims priority of U.S. provisional patent application entitled "METHOD AND APPARATUS FOR THE THERMAL/MECHANICAL TREATMENT OF METALLIC SPECIMENS", filed Jun. 26, 2003 and assigned Ser. No. 60/482,623; which is incorporated by reference herein.

CROSS-REFERENCE TO RELATED APPLICATION

This application describes and claims subject matter that is also described in our co-pending United States patent application entitled "APPARATUS FOR PROVIDING ENHANCED SELF-RESISTIVE SPECIMEN HEATING IN DYNAMIC MATERIAL TESTING SYSTEMS AND AN ACCOMPANYING METHOD FOR USE THEREIN", which is filed simultaneously herewith.

BACKGROUND OF THE INVENTION

1. Field of the Invention

The invention relates to apparatus, and an accompanying method for use therein, for use in a conventional dynamic thermo-mechanical material testing system in order to advantageously provide enhanced self-resistive specimen heating that yields greater temperature uniformity throughout a specimen under test than heretofore achieved.

Advantageously, our invention also finds use in a conventional dynamic mechanical material testing system in order to self-resistively heat a test specimen uniformly over its entire volume. Such heating can be controlled and synchronized to a mechanical test program, e.g., a pre-defined series of mechanical deformations, to impart a desired thermo-mechanical test program to the specimen for use in physical simulation and/or other material testing applications.

2. Description of the Prior Art

Metallic materials play an indispensable role as an essential component of an enormous number of different products and hence occupy an extremely important part of the world economy. As such, during manufacturing, various properties and costs of these materials need to be carefully controlled to maximize their utility and value in a given application.

Different metallic materials possess widely varying mechanical, metallurgical and other properties. Different applications necessitate use of materials with different properties. The specific properties required of a material for use in a given application are first determined followed by selection of a specific material that exhibits appropriate values of these properties.

During their initial production, metallic materials are generally formed into slabs or ingots and then from there controllably deformed into standard sized sheets, rods or coils using, e.g., conventional rolling, forging and/or extruding operations. However, correctly configuring a rolling mill, forge or extruder to properly deform production stock and impart desired physical and/or metallurgical characteristics to the material can be a tedious, time-consuming and expensive process—particularly since a production machine needs to be taken out of productive use for an extended time to properly adjust its operational parameters. Consequently, to avoid such downtime, the art teaches the general concept of determining properties of interest by testing relatively small specimens of each such material under consideration. One such technique for doing so is so-called "physical simulation". Ideally speaking, this technique, through use of a dynamic material testing system, permits each such specimen to undergo appropriate mechanical deformation and, where appropriate, simultaneous thermal processing that, collectively speaking and to the extent possible, accurately mimic, in a small-scale environment, strains and other phenomena that the same material (but of a far larger scale) would experience through an actual production operation, such as rolling, extrusion or forging. Such simulations, when accurately done, permit proper operational parameters of corresponding production machinery to be readily ascertained and, concomitantly, minimize non-productive downtime and its associated high costs.

One crucial property of metallic materials is their ability to conduct electricity. Absent operation at superconductive temperatures, a metallic object possesses a resistance to electrical current flow proportional to its length and resistivity and inversely proportional to its cross-sectional area. Owing to its resistance, the object will generate heat whenever an electric current is passed through it. This form of heating, i.e., so-called "self-resistive heating", finds use in a wide number of diverse applications. To the extent relevant here, dynamic material thermo-mechanical material testing systems can employ self-resistive heating to impart a desired thermal profile to each specimen prior to its being deformed in order to more accurately simulate material temperatures that will be experienced during a production operation.

Generally, in a conventional dynamic thermo-mechanical material testing system, a compressive specimen is held between two anvils or, in the case of a tensile specimen, gripped at each of its two ends in a jaw system. Since the following discussion applies equally well to both compressive and tensile testing, for simplicity, we will simply confine that discussion to compression testing.

For compression testing, the specimen is typically in the form of, for example, a small cylinder of a given material and has a substantially uniform circular cross-sectional area. Such specimens may be on the order of, e.g., 10 mm in diameter and 15 mm long; though other sizes are readily used as well. An electric current is serially passed from one anvil to another and hence generally cross-wise end-to-end through the specimen to generate a rapid, but controlled, heating rate throughout the specimen. Simultaneously therewith, various measurements are made of the specimen. Depending upon the specific measurements being made, the specimen either may or may not undergo controlled compressive deformation while it is being heated. If the specimen is to be deformed, then this deformation can be accomplished by moving one of the two anvils, at a controlled rate with respect to the other, in order to squeeze the specimen by imparting a given compressive force to the specimen. This process may be repeated several times, at differing amounts and rates of deformation, in order to impart a succession of different deformations to the specimen, thus yielding differing and accumulating amounts of strain in the specimen. Physical measurements, such as illustratively specimen dilation and temperature, are typically made while heating or cooling and deformation are simultaneously occurring. This testing not only reveals various static properties of the specimen material itself, such as its continuous heating transformation curve, but also various dynamic properties, such as illustratively hot stress vs. strain rates and hot ductility; the dynamic properties being particularly useful in quantifying the behavior of the material that will likely occur during rolling, forging, extrusion or other material forming and/or joining operations. One system that provides excellent dynamic thermo-mechanical testing is the GLEEBLE 3500 system manufactured by the Dynamic Systems, Inc. of Poestenkill, N.Y. (which also owns the registered trademark "GLEEBLE" and is the present assignee). Advantageously, this system self-resistively heats the specimen in order to generate transverse, essentially isothermal planes along the entire specimen, i.e., the specimen material in each plane uniformly heats as current passes longitudinally through that plane of the specimen. Consequently, density of the electrical heating current will be relatively uniform throughout that cross-section and, as such, will cause substantially uniform heating over that entire cross-section. Examples of such systems are described in the following United States patents, all of which are incorporated by reference herein: U.S. Pat. No. 6,422,090 (issued to H. S. Ferguson on Jul. 23, 2002); U.S. Pat. No. 5,195,378 (issued to H. S. Ferguson on Mar. 23, 1993); and U.S. Pat. No. 5,092,179 (issued to H. S. Ferguson on Mar. 3, 1992).

In such systems, the anvils need to withstand the relatively high forces imparted to the specimen without noticeably deforming themselves. Hence, these anvils are physically much larger and considerably more massive than the specimens. Consequently, for a given amount of self-resistive heating current serially passing through both the anvils and the specimen, the anvils will attain a much lower temperature than the specimen. As a result, longitudinal temperature gradients will appear end-to-end along the specimen, with a central work zone of the specimen being hottest and specimen temperature falling off towards each anvil—even though the self-resistive heating currents cause essentially isothermal planes to occur transversely across the specimen. These gradients tend to limit the work zone of the specimen to its central region, thus decreasing the effective length of the specimen for the simple reason that the hotter work zone tends to increasingly soften and deform before the cooler regions near the specimen ends do. This, in turn, tends to limit the maximum amount that the specimen can be compressed during each deformation and hence the maximum strain and strain rate that could be imparted to the specimen.

To eliminate these longitudinal gradients, conventional anvil assemblies can be self-heated or separately heated. Unfortunately, owing to the relatively large mass of the anvils compared to the specimen, the heating time of the anvils would be considerably larger than that of the specimen which, in turn, limits a maximum rate at which the specimen could be heated. This, in turn, slows the thermal response of the entire system and is particularly problematic if more than one test temperature is required for a given thermo-mechanical program, i.e., each successive deformation ("hit") is to be performed at a different specimen temperature. Specifically, this requires that the anvils reach thermal equilibrium at each such successive programmed temperature before each hit occurs. Depending on the temperature excursions involved, the required anvil heating or cooling times could drastically slow the overall response of the system. Modern material production equipment, such as multi-stand rolling mills, often dynamically deforms materials at relatively high-speeds. Hence, any appreciable diminution in the response of the test system, such as those imposed by limits associated with the anvil heating and cooling rates, could severely and adversely limit the production processes that could be accurately simulated by such systems, thus potentially diminishing the attractiveness and cost-efficiencies otherwise attainable through use of such systems.

As increasingly high-speed production processes are currently being employed in industry, a concomitant need has recently arisen with conventional thermo-mechanical material testing systems to impart increasingly higher amounts of strain and strain rates to specimens. Therefore, a need exists in the art for another approach which can be used in such systems for substantially, if not totally, eliminating longitudinal thermal gradients from appearing in self-resistively heated test specimens that are held in anvils (and jaw assemblies). Ideally, such an approach should not appreciably slow the response of the system but still yield isothermal planes in the specimens.

To address this need, the art teaches one approach to substantially eliminate these thermal gradients; namely, by generating sufficient self-resistive heat within each anvil to approximately equal that which would otherwise flow from the specimen into the anvil. This, in turn, would eliminate much, if not substantially all, of any temperature difference otherwise occurring between a top surface of each anvil and the specimen bulk and hence preclude any appreciable longitudinal thermal gradients from appearing in the specimen.

To effectuate this approach, the art teaches that each anvil can be formed of an anvil stack having cylindrically shaped upper and lower members separated by a foil interface having relatively high-resistance compared to the anvil. The sides of the anvil stack are electrically and thermally insulated from its supporting structure by a suitable insulating member, typically a woven ceramic tubing or rigid ceramic sleeve. As a result and during one-half cycle of applied current, self-resistive heating current axially flows up from the support through a base of the anvil stack, through the high-resistive foil interface, through an anvil top and into the specimen end (and in an opposite direction during a next half-cycle of applied current). Since the resistance of the foil interface is relatively high compared to the anvil, passage of the heating current through the foil interface causes it to self-resistively heat with the heat propagating throughout the entire anvil, including the anvil top. The foil interface is typically formed of a stack having a predefined number of graphite disks, with each disk being of an approximate diameter of the anvil and of a given thickness to provide a desired resistance. Unfortunately, the graphite disks, when exposed to the rather high impact forces transmitted to the anvil stack during each hit, are rather compliant and tend to deform and unevenly so, from one disk to the next, from each impact. The result is that the abutting electrical contact amongst the graphite disks as well as the resistance of each disk changes with each hit which, in turn, adversely affects the passage of heating current and hence the heating of the specimen.

Therefore, a need still exists in the art for an approach, for use in a dynamic thermo-mechanical material testing system, that can effectively and substantially, if not totally, eliminate thermal gradients from appearing in a specimen then under test while still permitting isothermal planes to occur in the specimen, but without deforming, to any appreciable extent, if at all, under the high impact force generated during each hit.

Furthermore, a considerable number of conventional, commercially available dynamic material testing systems only provide mechanical deformation of the specimen without any capability of thermally processing of the specimen. These systems basically only compress a specimen held end-to-end between two anvils which are themselves moved by a servo-hydraulic or screw driven actuators to controllably squeeze the specimen. However, to accurately simulate production processes, the specimen under test needs to undergo controlled uniform thermal processing synchronized to the occurrence of the mechanical deformations. As such, these systems need to be modified, by the addition of appropriate apparatus, to possess the capability of providing accurate self-resistive specimen heating that establishes isothermal planes across the specimen under test but without causing appreciable, if any, longitudinal temperature gradients to appear along that specimen. Here too, this apparatus should not deform, to any appreciable extent, if at all, under the high impact force generated during each hit. Hence, a need also exists in the art to provide these capabilities in such conventional mechanical testing systems.

Should these needs be met, then, the attractiveness of physically simulating high-speed production processes through dynamic material testing equipment could very well increase, with advantageously substantial cost savings flowing there from to their users.

SUMMARY OF THE INVENTION

The present invention advantageously overcomes the deficiencies in the art by incorporating, into each anvil assembly between an anvil base and an anvil top, a foil interface that has at least one multi-component composite layer, with each constituent component therein having specific but differing thermal, electrical and mechanical properties from the other.

This composite layer, generally in the shape of a disk and in its preferred embodiment, is preferably concentrically oriented and illustratively formed from two disks of different materials, but of the same thickness, with one fitting within the other. One disk, being a thermal and electrical insulator but with high compressive strength, forms a central portion of the composite layer; while the other disk, being electrically resistive, forms an outer ring portion concentrically situated around and peripherally abutting the outer surface of the central portion. Electrical current only flows through the outer ring portion and causes that portion to self-resistively heat, while the central portion provides high impact strength and hence substantial resistance to deformation, thus preventing the outer ring portion from deforming as a result of a hit. Illustratively, the central portion is formed of a mica disk and the outer ring portion is formed of a graphite ring. In fabricating the foil interface to have the proper resistance and hence heating characteristics, the composite layer may be replicated as often as necessary with suitable conductive disk, typically of tantalum (or other suitable conductive material), placed between successive composite layers (in the shape of disks), for use within a given anvil stack. Furthermore, all the layers within the stack need not have the same thickness, as one or more may have differing thicknesses, in order to properly set the resistance of the entire foil interface. Also, the materials used for the central and outer-ring portions may be reversed such that the central portion is conductive, e.g., formed of graphite, while the outer ring-shaped portion is formed of the high strength insulating material, e.g., mica. The sides of the anvil stack are electrically and thermally insulated from its supporting structure by a suitable insulating member, typically a woven ceramic tubing or rigid ceramic sleeve.

The inventive anvil assembly can simply replace existing anvil assemblies used in conventional dynamic thermo-mechanical material testing systems in order to beneficially and advantageously impart substantially uniform self-resistive heating, throughout the specimen bulk, that exhibits isothermal planes but without any appreciable longitudinal thermal gradients appearing and without appreciably deforming, if at all, as a result of each hit.

Furthermore, our inventive anvil assembly can also be readily incorporated into conventional mechanical testing systems that lack a capability to thermally process the specimen in order to provide the same benefits as would arise through use of these anvil assemblies in a dynamic thermo-mechanical material testing system.

To do so, a separate fixture, in accordance with our inventive teachings, is added to these mechanical testing systems. The fixture includes two opposing inventive coaxially-oriented anvil assemblies, which collectively hold the specimen and exerts sufficient force, through the anvils, onto the specimen to permit self-resistive heating current to serially pass through the anvils and the specimen for heating the specimen. This fixture utilizes separate supporting arms, each of which holds a corresponding one of the anvil assemblies, situated on opposing sides of the specimen. The fixture, through the action of springs, pneumatic cylinders or a combination thereof, applies force to each arm sufficient to hold the specimen in position between the opposing anvil assemblies and establish a good abutting electrical contact therebetween, which permits the current to flow through the specimen but without causing substantially any arcing, but with insufficient force to deform the specimen as it is being heated. Separate opposing coaxially-oriented shafts (rams) existing within these systems which heretofore were extended to simply squeeze the specimen itself are instead controllably extended to strike the arms and squeeze them together, hence squeezing the anvils together, to, in turn, generate each deformation "hit" in the specimen. At the conclusion of each hit, these shafts are suitably retracted in preparation for the next such hit on the fixture and hence on the specimen. The shafts are electrically insulated from the fixture so that the self-resistive heating current can be controllably and serially applied just through the fixture arms, the anvil assemblies and specimen. Controlled current flow can occur before, during or after each hit to appropriately and uniformly heat the specimen bulk to a desired temperature at the appropriate time in its test procedure.

The inventive fixture can be easily retrofitted to nearly any commercially available mechanical testing system by simply being mounted, e.g., within a suitable vacuum/atmospheric tank, to existing supporting columns in those systems, and preferably within a central working region of the system, to permit an equal working extension of the existing shafts.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

After considering the following description, those skilled in the art will clearly realize that the broad teachings of the invention can be readily utilized in conjunction with a wide variety of material testing systems, including both dynamic mechanical and thermo-mechanical material testing systems, that controllably deform a test specimen to permit such systems to implement complex thermal and mechanical programs for use in simulating a wide variety of production processes and material applications. For simplicity, we will discuss our invention in the context of its incorporation and use within a relatively simple and generic dynamic mechanical material testing system. Based on that description, any one of skill in the art can readily and easily ascertain how the teachings of our invention can advantageously be incorporated into any one of a wide variety of existing thermo-mechanical material testing systems.

Figure 1:
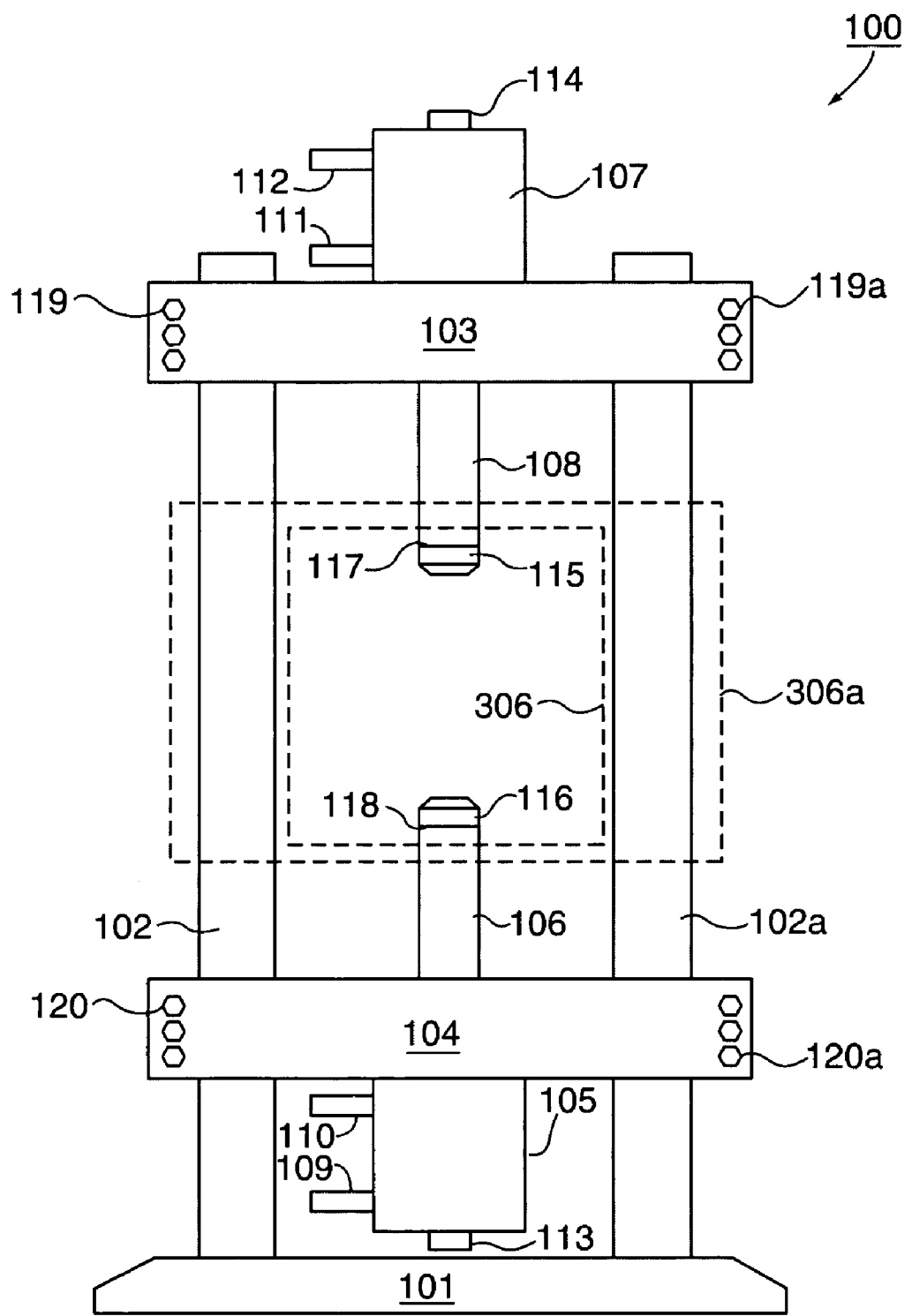
FIG. 1 depicts, in side view, conventional, commercially available dual-ram servo-hydraulic mechanical testing system 100.

FIG. 1 depicts, in side-view, commercially available servo-hydraulic mechanical material testing system 100.

As depicted, system 100 is comprised of a frame illustratively formed of base 101, columns 102 and 102a, upper crosshead 103 and lower crosshead 104. The system also contains lower hydraulic cylinder 105 and its shaft 106, and upper hydraulic cylinder 107 and its shaft 108. Crossheads 103 and 104 are split vertically at their horizontal ends extending inward to the columns. Bolts 119 and 119a, and 120 and 120a, extending through their corresponding crossheads, fixedly clamp crosshead 103 and 104, respectively, to the columns.

As shown, this system has two hydraulic cylinders 105 and 107, as contrasted with many conventional systems that have only one cylinder usually situated on lower crosshead 104. Lower cylinder 105 is mounted to a bottom surface of lower crosshead 104 such that companion shaft 106 extends upward from the cylinder through a hole (not specifically shown) in this crosshead. Upper cylinder 107 is mounted to an upper surface of upper crosshead 103 such that its companion shaft extends downward from this cylinder through a hole (also not shown) in the upper crosshead. Hydraulic connections 109 and 110, 111 and 112 with suitable hydraulic hoses (not specifically shown) connect cylinders 105 and 107, respectively, to separate corresponding servo-hydraulic control systems (also not shown). These two servo-hydraulic control systems are of a type commonly used in controlling servo-hydraulic testing machines and are very well known in the art; hence, they will not be described in any further detail. Feedback transducers 113 and 114, mounted to cylinders 105 and 107, respectively, provide shaft position information to the servo-hydraulic systems for use in controlling the movement of the shafts. Although this figure contemplates the use of servo-hydraulic controlled cylinders 105 and 107 for positioning shafts 106 and 108, these cylinders could be replaced with other suitable mechanical actuators, such as ball screws, with appropriate position transducers and servo-control systems, that collectively provide suitable actuator movement and can apply suitable forces there through to corresponding anvils for deforming a specimen.

Area 306, generally centrally located and situated between columns 102 and 102a, could contain a vacuum/atmospheric tank (not specifically shown) with the inventive apparatus mounted inside the tank. Alternately, area 306a, which is larger than area 306, includes part of columns 102 and 102a and affords space, within the tank, to mount the inventive apparatus to the columns. In both cases, the apparatus is centered vertically between shafts 106 and 108 (i.e., in an approximate central working region of the system) and fixedly mounted to the columns (either internally as in the case of area 306a or externally in the case of area 306). A mechanical system that employs only one hydraulic cylinder, such as cylinder 105, would require that the apparatus be oriented vertically off-center, within area 306 or 306a, such that an anvil mounting base, situated opposite an end of shaft 106, would be mounted to a rigid shaft (not specifically shown but well known) rather than to a ram situated on an end of a shaft. In this instance, shaft 106 would simply drive its ram toward the anvil mounted to the rigid shaft, hence moving both anvils closer together. Shaft caps 115 and 116 are provided at the ends of shafts 108 and 106, respectively, to abuttingly engage suitable and corresponding anvil mounting bases (not specifically shown in this figure). Caps 115 and 116 are situated on but are electrically isolated from shafts 108 and 106 by insulators 117 and 118, respectively. Each of shafts 106 and 108 is formed from preferably austenitic stainless steel or 17-4 Ph heat treated stainless steel. Caps 115 and 116 are preferably formed of 17-4 Ph heat treated stainless steel. Insulators 117 and 118 are preferably fabricated of fiberglass, such as grade G-10, which has adequate compressive strength to withstand a maximum force provided by servo-hydraulically controlled cylinders 105 and 107 attached to distal ends of the shafts.

Figure 2:
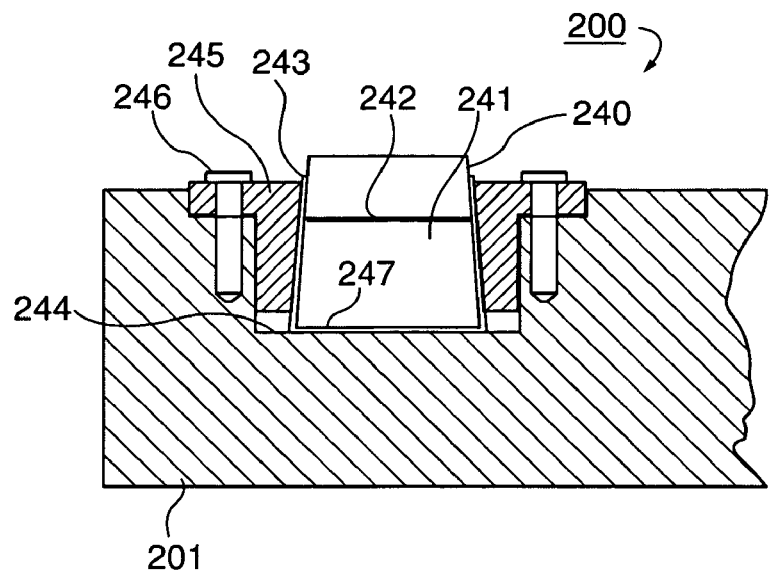
FIG. 2 depicts, in a sectional view and taken along lines 2—2 shown in FIG. 4, self-resistively heated anvil assembly 200 that incorporates the teachings of the present invention.
Figure 4:
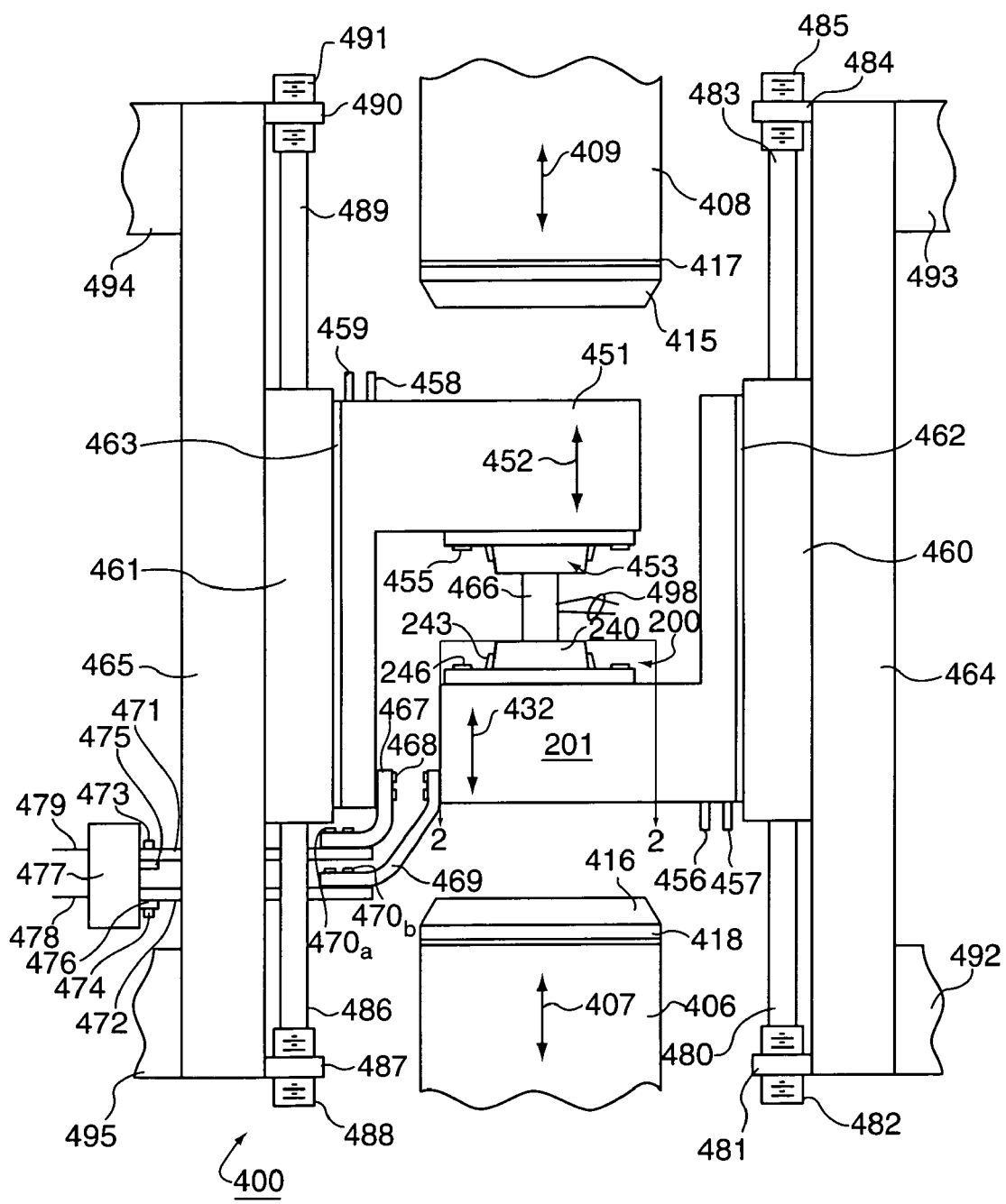
FIG. 4 depicts, also in side view, fixture 400, that incorporates the teachings of our present invention including anvil assembly 200 shown in FIG. 2, which would be incorporated into the conventional system shown in FIG. 1.

FIG. 2 depicts a cross-sectional view of self-resistive anvil assembly 200 according to our inventive teachings, taken along lines 2—2 shown in FIG. 4 and located along a centerline of the assembly, which prevents nearly, if not totally, all longitudinal thermal gradients from appearing in a test specimen held by the anvils as that specimen undergoes self-resistive heating. A dynamic material testing system that utilizes our invention would employ two such anvil assemblies. Since both assemblies are identical, we will merely discuss one of them.

As shown, anvil assembly 200 is mounted in support arm 201. Anvil top 240 is mounted on anvil base 241 with at least one relatively high-resistance foil interface 242 situated there between. Foil interface 242 (which is illustratively shown in greater detail in FIG. 3 and will be described in detail below shortly) can be formed from any of a number of different substances, such as graphite, tantalum, mica or other well-known materials, that exhibit suitable electrical resistance and other electrical properties, as well as appropriate mechanical properties. The exact material used for the foil interface, as well as the number of layers that fabricate foil interface 242, are not critical. The anvil top and base are each typically formed of a high strength material, such as tungsten carbide with a cobalt binder. The cobalt binder is appropriately varied, in its amount, to change the properties of the anvil material and is usually in the range of 6 to 12 percent of a resulting composite. A composite in this range produces a high temperature material which retains its high strength at relatively high temperatures.

A resulting anvil stack consisting of anvil top 240, anvil base 241 and foil interface 242 is tapered with an substantially upward sloping conical taper to allow vertical mounting as shown, as well as inverted mounting (opposite to that shown). The substantially conical shape imparts enhanced mechanical stability to the stack. The stack is held together by and includes holder 243, preferably either ceramic woven tubing or a rigid ceramic sleeve, that is tightly placed circumferentially around the stack. The anvil stack is placed within cavity 244 in the support arm. Tapered clamp 245, which has a taper complementary to that of the holder, secures the stack including its holder to the arm. The holder, whether it is a woven ceramic tubing or a rigid ceramic sleeve, substantially thermally and electrically insulates the anvil stack from clamp 245. Clamp 245 is itself secured in place to arm 201 by fasteners (generally suitable bolts) 246.

The anvil stack is heated by serially passing electrical heating current through the constituent components of the anvil stack and the specimen. To prevent foil interface 242, specifically any of its layers, from deforming under the forces it encounters during each hit, foil interface 242 is fabricated from materials that are sufficiently hard to resist deformation as well as provide sufficient resistance to self-resistively heat to a sufficient level to prevent appreciable, if any, heat conduction from an end of the specimen under test into the top anvil. The ceramic insulation, provided by holder 243, on the sides of the anvil stack allows current flow only through arm 201, through the bottom of anvil base 241 and upward through anvil stack to specimen 466 (specifically shown in FIG. 4). To enhance abutting electrical contact between the anvil stack and support 201, a single soft thin disk 247, typically copper, is situated between the anvil base and a lower surface of cavity 244.

Foil interface 242, which serves as an interface between the anvil top 240 and anvil base 241 of the stack, exhibits a sufficiently high electrical resistance in order to cause substantial self-resistive heating at the interface. When heating current serially passes through the anvil and specimen, ideally, sufficient heat is produced by the foil interface and propagates through anvil top 242 to cause the temperature of the anvil top to be at or very close to the temperature of the specimen bulk, thereby precluding heat transfer from the specimen to the anvil top. The temperature of the anvil top can be readily adjusted by changing foil interface 242 by adding or subtracting individual foil interface layers and/or changing the material of the foil interface layers to adjust the overall resistance of the foil interface and thus adjust the thermal profile produced in the anvil top. When the resistance and hence the configuration and the materials of the foil interface are properly set, the thermal profile along the specimen will be relatively flat or at a constant temperature, when the ends of the specimen are in contact with anvils (both the anvil stack situated on one side of the specimen and its complementary stack abutting against an opposite end of the specimen) at the same temperature. Consequently, this substantially, if not totally, eliminates any thermal gradients from appearing in the specimen bulk and particularly in the region between the work zone of a specimen and its end that abuts against a top surface of a corresponding anvil top.

Figure 3:
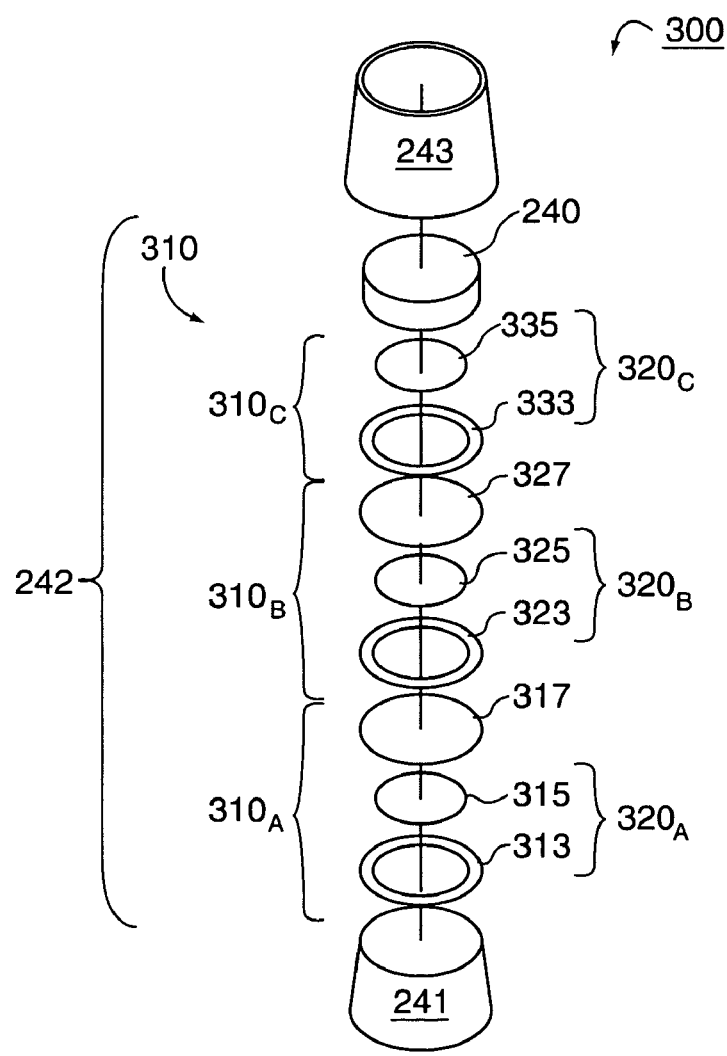
FIG. 3 depicts, in accordance with our invention and in exploded view, illustrative anvil stack 300 that forms part of anvil assembly 200 shown in FIG. 2.

FIG. 3 depicts, in accordance with our invention, an illustrative embodiment of anvil stack 300 which forms part of anvil assembly 200 shown in FIG. 2, with foil interface 242 shown in an exploded view. As shown, anvil stack 300, as with that shown in FIG. 2, is formed of anvil base 241, foil interface 242 and anvil top 240, which are all contained within holder 243 here being a sleeve insulator. This sleeve, is illustratively a Nextel sleeve which is a woven high-temperature cloth fiber insulator which reduces temperature loss to clamp 245 (See FIG. 2) and provides electrical insulation on the sides of the anvil.

We have discovered, in accordance with our inventive teachings, and empirically confirmed that excellent and uniform specimen heating and high impact resistance can be had by use of at least one composite layer in foil interface 242 with a concentrically oriented multi-component arrangement. Specifically, that composite layer is formed from two disks of different materials, but of the same thickness, with one fitting within the other. One disk being a thermal and electrical insulator but with high compressive strength, forms a central portion of the composite layer; while the other disk, being electrically resistive, is appropriately shaped to form an outer ring portion and is concentrically situated around and peripherally abutting the central portion. The resulting composite layer is a single solid disk, formed of two abutting concentrically aligned portions, that collectively exhibits significantly differing mechanical, thermal and electrical properties between its outer ring and central portions. Electrical current only flows through the outer ring portion and causes that portion to self-resistively heat, while the central portion provides high impact strength and hence substantial resistance to deformation thus preventing the ring-shaped portion and the entire composite layer from deforming as a result of a hit and changing the resistance of the conducting path through the outer ring portion. Alternatively, the materials used for the central and outer ring portions may be reversed such that the central portion is resistive, e.g., made of graphite, while the outer ring portion is formed of the insulating, high-strength material, e.g., mica. In this case, the outer ring portion prevents deformation of the central conductive portion during each hit. In either case, the outer ring size and diameter of the central portion are appropriately chosen to obtain suitable thermal, mechanical and electrical characteristics for these portions based on the specific materials that form these portions.

As specifically shown in FIG. 3, foil interface 242 is formed of three layered foil interface groupings $310_A$, $310_B$ and $310_C$, of which foil interface groupings $310_A$ and $310_B$ are identical. For simplicity, we will specifically discuss foil interface grouping $310_A$. Grouping $310_A$ contains ring portion 313, central portion 315, both of which form a single composite layer $320_A$, and disk 317 situated there above. Central portion 315, having a diameter on the order of 0.75" (approximately 1.9 cm) is formed of illustratively a solid mica disk which acts as both a thermal and electrical insulator, and can withstand very high compressive forces without deforming. This mica disk is approximately 0.004" thick (approximately 0.01 cm). Outer ring portion 313, of the same thickness, is formed of graphite having an inner diameter of 0.75" and an outer diameter of approximately 1" (approximately 2.5 cm). Disk 317 is preferably a solid tantalum foil disk with a 1" outer diameter and 0.004" thickness. Foil interface grouping $310_B$ is formed of outer ring portion 323 and central portion 325 (which together form composite layer $320_B$) and disk 327—which are identical to ring portion 313 and central portion 315 (and composite layer $320_A$), and disk 317. Foil interface grouping $310_C$ is identical to foil interface groupings $310_B$ and $310_A$ but without a top tantalum disk, e.g., such as disk 327. The resulting composite layer $320_C$ formed of outer ring portion 333 and central portion 335 merely, as the top of foil interface 242, abuts against an underside of anvil top 240. Using multiple foil interface groupings to form foil interface 242 creates additional resistance and hence heating in the anvil. The dimensions and materials and number of individual foil interface groupings and the number of individual layers in each is not critical as long as the entire resulting foil interface, here foil interface 242, exhibits sufficient electrical resistance to generate an appropriate level of heat within the anvil stack to offset self-resistive heat that would otherwise flow from an end of the specimen under test into its abutting anvil top. While mica, graphite and tantalum are specifically employed here, other materials with similar electrical, mechanical and thermal characteristics could be substituted instead, though sized accordingly.

Furthermore, while the composite layer is illustratively shown as constituted of concentrically oriented central disk and outer ring portions formed from just two disks, e.g., disks 315 and 313, respectively, clearly other arrangements for the composite layer can be contemplated that exhibit other geometries. One such geometry may envision a relatively large single disk of conductive material, such as graphite, that has either, e.g., circular, triangular and/or rectilinear cutouts there through in which complementary and correspondingly sized pieces of high strength, insulating material, such as mica, are placed. Furthermore, different materials may be placed in different cutouts to suitably alter the desired properties of the entire composite layer. While we have empirically found that concentric arrangements of the type described above for the composite layer provide highly satisfactory results and are relatively simple to manufacture, we also recognize that equal performance may be obtained from other composite layer geometries whether concentric or not. Nevertheless, however configured, the resulting composite layer must possess the requisite thermal, mechanical and electrical properties in terms of electrical resistivity/insulation and/or high strength such that the entire anvil stack yields the desired heating, conductivity and high strength to impact forces.

FIG. 4 depicts, also in side view, our present invention, including anvil assembly 200 shown in FIG. 2 along with accompanying apparatus, that would be incorporated into conventional mechanical testing system 100 shown in FIG. 1.

In accordance with our further inventive teachings, the specimen is held in a separate supporting fixture which includes the anvil assembly and exerts sufficient force (in opposing directions), through the anvils, onto the specimen to permit self-resistive heating current to serially pass through the anvils and the specimen for heating the specimen. This fixture utilizes separate supporting arms, each of which holds an anvil assembly, situated on opposing sides of the specimen. The fixture applies force to each arm to sufficiently hold the specimen in position between opposing anvil assemblies and permit the heating current to flow through the specimen without causing substantially any arcing but with insufficient force to deform the specimen as it is heated. Separate opposing coaxially-oriented shafts are then controllably extended to controllably strike the arms and move them together to compress the specimen and, as such, generate each deformation "hit" in the specimen. At the conclusion of each hit, these shafts are suitably retracted in preparation for the next such hit. Inasmuch as the shafts are electrically insulated from the fixture, self-resistive heating current can be controllably and serially applied through the fixture arms, the anvil assemblies and specimen before, during or after each hit to appropriately and uniformly heat the specimen bulk to a desired temperature. Since such a fixture can be easily retrofitted to nearly any commercially available mechanical testing system, our invention uniquely imparts self-resistive heating capability to such systems, and particularly through use of our inventive anvil assembly, uniformly heats the specimen to produce isothermal planes therein and without appreciable, if any, thermal gradients appearing along the specimen length. This fixture is not needed in a dynamic material testing system that already provides self-resistive heating capability. In that instance, use of our inventive anvil assembly alone will suffice to provide uniform specimen heating along with isothermal planes, and without longitudinal thermal gradients, throughout the specimen bulk.

Specifically and as shown, fixture 400, including the anvil assembly, is fixedly, vertically and centrally mounted between lower shaft 406, with shaft cap 416, and upper shaft 408 with shaft cap 415. Shafts 406 and 408 move, under servo-hydraulic control in the directions shown by arrows 407 and 409, respectively. To prevent heating current from traveling through the shafts, shaft caps 415 and 416 are electrically insulated, by insulators 417 and 418, from shafts 408 and 406, respectively.

This fixture is formed of support arms 201 and 451 that are each constrained to move vertically up or down but independently of the other. Heating current flows through each of the arms. Support arms 201 and 451 have anvil assemblies 200 and 453 mounted in respective cavities (see FIG. 2 for cavity 244 in arm 201) and secured with fasteners 455 and 246, respectively. The anvil assemblies are coaxially oriented. Each of the support arms is fabricated from a sufficiently strong material which will endure repeated hitting at high force without deforming. Typically, these support arms are made from a 303 or 304 series stainless steel or 17-4 Ph heat-treated stainless steel. Both support arms 201 and 451 are water cooled to prevent the arms and the components to which they are physically connected from excessively heating due to the self-resistive heating of the anvil stacks and the specimen, as well as any self-resistive heating that may occur within the arms themselves due to the passage of heating current there through. Water ports 456 and 457 provide connections to the water cooling passages (not specifically shown) in arms 201, while water ports 458 and 459 provide connections to water cooling passages (also not specifically shown) in arm 451.

Support arms 201 and 451 are secured to slide plates 460 and 461 through insulation plates 462 and 463, respectively, using conventional insulated fasteners (not shown). Slide plates 460 and 461 are free to move vertically up and down along system mounting rails 464 and 465, being connected therebetween through suitable pairs of linear bearings (conventional and not shown) which guide this vertical motion. The rails and slide plates collectively form a mount for the support arms. As such, arms 201 and 451 move in the vertical directions shown by arrows 432 and 452, respectively. The slide plates are mounted to rails 464 and 465 through any of the many linear slide mechanisms readily available in the commercial market place and which would restrict the motion of the slide plates to just vertical motion. The linear bearings are used in side-by-side pairs to restrict this motion to a single plane. This arrangement also permits support arms 201 and 451, anvil assemblies 200 and 453 and specimen 466 situated therebetween to collectively and freely move vertically up and down as a single unit. Additionally, arms 201 and 451, by moving independently of one another, permit specimen 466 to be appropriately positioned therebetween and then to be compressed. Mounting rails 464 and 465 may be mounted to the inside of a vacuum/atmospheric tank or to the columns 102 and 102a (see FIG. 1). As shown in FIG. 4, rails 464 and 465 are themselves rigidly mounted to mounting brackets 492 and 493, and 494 and 495, respectively. The brackets are suitably fashioned to attach the rails to the tank walls or to columns 102 and 102*a* (see FIG. 1).

Electrical heating current for self-resistively heating specimen 466 is supplied by transformer 477 and flows in a simple series path. Though not critical, the transformer should possess a 440 volt, single phase 75 kVA primary with a 5.7 to 10 volt paralleled secondary, preferably controlled by a tap switch, and a 50 or 60 Hz operating frequency. The short circuit output current should be on the order of 50 kA or more. The secondary winding of the transformer is typically formed of one or two turns of a heavy copper casting. By varying the turns ratio of the transformer in finite increments through the tap switch, specimens of different sizes and shapes can be readily heated. Such a transformer is the model G4475NS61S manufactured by Kirkhof Transformer of Grand Rapids, Mich. Transformer 477 is connected to a suitable and conventional servo controlled power source (not shown) via leads 478 and 479.

The current path, for one-half cycle of alternating current flow, starts at transformer output stab 475 and from there continues into bus 471. This bus is connected, via fasteners 473, to the stab. From bus 471, the current flows into one end of flexible conductor 467 which itself is physically and electrically connected, through fasteners 470*a*, to the bus. Bus 467 is connected, via fasteners 468, to arm 451 and hence the heating current is routed into this arm. From the arm, the heating current is directed through anvil assembly 453 and into specimen 466. Once the current passes through the specimen, it traverses through anvil assembly 200 into support arm 201. This arm is itself electrically connected through flexible conductor 469, to bus 472. Bus 472 is itself connected, via fasteners 470*b*, to conductor 469 and, via fasteners 474, to output stab 476 of the transformer. Hence, the heating current will flow from arm 201, through flexible conductor 469, into bus 472 and finally, via stab 476, back into the transformer. The current flow will simply reverse its direction for the other half cycle of current flow. The bus, flexible conductors, support arms, anvil bases and anvil tops all have extremely low electrical resistance. Therefore, almost all of the heating occurs in specimen 466 and in the anvil stack, specifically within foil interface 242 situated within each stack. The water cooling removes heat that occurs in the other components of fixture 400 that are physically and thermally connected to the anvil assemblies.

The self-resistance heating is controlled through a conventional servo-control system which utilizes feedback from a thermocouple having output leads 498 and which is affixed to a work zone of the specimen 466. A suitable pyrometer may be used instead of the thermocouple. Output feedback signals provided by either the thermocouple or the pyrometer (whichever is used) is provided as input, through appropriate conventional signal conditioning circuitry, to an input of the servo-control system. Generally speaking, the servo-control system has a predefined program of temperature vs. time. The thermocouple output is compared continuously with the program, and the power to the transformer is then adjusted to keep the specimen temperature as close as possible to that desired and specified in the temperature program. The thermal program is typically synchronized to a mechanical program to provide complete thermal/mechanical control over the specimen. The servo-control system is very similar to those used in the "GLEEBLE" material testing systems produced by the present assignee and as described in illustratively U.S. Pat. No. 6,442,090 (issued to H. S. Ferguson on Jul. 23, 2002); U.S. Pat. No. 5,195,378 (issued to H. S. Ferguson on Mar. 23, 1993); and U.S. Pat. No. 5,092,179 (issued to H. S. Ferguson on Mar. 3, 1992). Given the conventional nature of these control systems, they will not be discussed in any further detail.

In order for specimen 466 be held in position and squeezed with adequate force to provide a good electrical path for the heating current through the anvil assemblies and the specimen, four springs are provided to apply forces to the top and bottom of slide plates 460 and 461. Two springs are employed to provide compressive force for plate 461, and the other two provide compressive force for plate 460.

Compression spring 480 is mounted between plate 460 and adjustment screw 482, which is threaded into internally threaded bracket 481. Adjusting the screw in or up causes spring 480 to increasingly compress and hence exert increased force onto slide plate 460 forcing the plate upward. Each of the three other springs 483, 486 and 489 are mounted and adjusted in a similar fashion through adjustment screws 485, 488 and 491 threaded into internally threaded brackets 484, 487 and 490, respectively. Since springs 480 and 489 provide the additional force (preload) to hold the specimen and maintain low enough electrical resistance for the heating current, these springs may be stronger than springs 483 and 486. The preload obtained from the forces of springs 480 and 489 minus any counter-balancing forces from springs 483 and 486 (net force) is the order of 200 to 600 N (newtons) depending on the specimen size. The net force on the specimen, while not critical, is chosen to be large enough to pass electrical current through the specimen without substantially any arcing occurring yet small enough so as not to deform the specimen while it remains at an elevated temperature. A centering force, collectively produced by all the springs, should be enough to compensate for the weight of the slide plates, support arms, the anvil assemblies and the specimen so that these components effectively "float" in approximately mid-position along mounting rails 464 and 465. The range of the desired centering force is the order of 50 to 100 N depending on the specimen size.

Alternatively, suitable conventional pneumatic cylinders (along with proper regulators and values), one for each slide plate, may be used in lieu of springs 480 and 483 and adjustment screws 482, 485, 488 and 491. Use of cylinders may be preferred inasmuch as spring force changes rapidly with deflection (unless an extremely long spring is used) and springs generally require more maintenance and must be mechanically adjusted to yield the proper forces. Furthermore, by simply and appropriately setting the pressure within each cylinder, the forces required to operate fixture 400 can be easily adjusted to an desired amount as can movement of the support arms and anvils to readily permit loading and unloading of the specimen. Since the force provided by shafts 406 and 408 onto support arms 201 and 451 during each hit substantially exceeds the specimen holding force provided by the fixture so as to controllably deform the specimen, the fixture must be resilient and permit the support arms to move together even while they are holding the specimen. For that reason, springs, pneumatic cylinders or other suitable force producing devices, which have inherent resilience, are preferred over other devices, such as ball screws, that could position the support arms and provide the requisite specimen holding force but exhibit essentially no resilience.

Two air regulators would maintain correct pneumatic pressure at all times regardless of the motion of cylinder rods pushing on slide plates 460 and 461. A typical installation would involve use of two air regulators, two pneumatic cylinders and two 4-way, 3-position center-port blocked pneumatic control valves. Any other suitable type of pneumatic valves can be used depending on the way the valves are connected and operated. A typical installation involves attaching one cylinder to bracket 484 and the other cylinder to bracket 490. An end of the cylinder rod of the cylinders pushes on plates 460 and 461. One air regulator is set to provide the desired compression force to maintain electrical contact between the anvils and the specimen during self-resistive heating. The other air pressure regulator is set to balance the weight of the assembly so that, in operation, the support arms remain relatively well-centered on the mounting rails.

To insert or remove the specimen from between the anvil assemblies, these assemblies, i.e., arms 201 and 451, must be moved sufficiently apart from each other to afford appropriate space between them for a user to suitably manipulate the specimen. If just spring force is used to control the motion of slide plates 460 and 461, then arms 201 and 451 must be separated manually using a suitable bar to overcome the force generated by the springs and thus provide sufficient space between the anvil assemblies to insert, position and remove the specimen. Alternatively, if pneumatic cylinders are used instead of springs, then the pneumatic control valves can simply be set to cause the support arms and hence the anvil assemblies to readily separate allowing the specimen to be easily inserted, positioned and subsequently removed. When the specimen is set in place, the pneumatic control valves are simply returned to their original position. Clearly, use of pneumatic cylinders greatly simplifies the process of loading and unloading the specimen over that required with springs.

After the specimen is loaded between the anvil assemblies and its thermocouple connected to the thermal servo-control system, appropriate thermal and mechanical programs are placed into the control system. Testing is then initiated and desired specimen measurements begun. Through doing so, the specimen is brought to its first deformation temperature at a programmed rate and through controlled self-resistance heating. The mechanical system then controllably moves shafts 406 and 408 to strike the support arms and through movement of opposing anvil assemblies 201 and 453 squeezes and compressively deforms the specimen at a programmed rate and amount. Once this deformation is complete, shafts 406 and 408 are then appropriately retracted. The specimen is then suitably heated or cooled at a programmed rate, and, thereafter, to implement a next successive deformation, the shafts are once again controllably moved to strike the support arms, and so forth.

Though we have described our inventive anvil assembly for use with specimens that undergo compressive deformations, our invention multi-component foil interface layer could be readily included within jaw assemblies for use with self-resistively heated specimens that are to undergo tensile deformations in order to provide, similarly with compressively deformed specimens, uniform heating throughout the specimen bulk. However, with tensile testing, there are no impact forces imparted to the specimen as the jaws are controlled to stretch the specimen apart by its ends, through tension, rather than compressing it. As such, there is no need to use a high strength component, for resisting impact forces, within any composite layer situated within the foil interface.

Furthermore, while we have described retrofitting a dynamic mechanical material testing system with our inventive fixture, that utilizes our inventive anvil assembly, to impart thermal processing capability to that system, through self-resistive specimen heating coupled with the above-described benefits attainable through use of that assembly, the fixture alternatively, if desired, could be outfitted with conventional conductive anvils instead. In that case, self-resistive specimen heating will still occur with isothermal planes developed in the specimen. Unfortunately, longitudinal thermal gradients may well appear in the specimen and near its ends.

Lastly, though we have described our inventive anvil assembly and fixture as being vertically oriented, they could alternatively be horizontally positioned for use with horizontally oriented material testing systems, the direction simply being governed by the direction of motion of the piston shafts (specifically rams) used in these systems to deform the specimen. Hence, those skilled in the art fully understand that when the term "vertical" is used herein, that term is merely being used in a relative sense and would, where appropriate, encompass horizontal orientations should the entire testing system be so oriented.

Although various embodiments which incorporate the teachings of the present invention have been shown and described in detail herein, those skilled in the art can readily devise many other varied embodiments that still incorporate these teachings.

We claim:

1. Apparatus for an anvil assembly (200) for use in a material testing system (100) which controllably deforms a specimen, the apparatus comprising:
    an anvil base (241);
    an anvil top (240); and
    a foil interface (242) situated between the anvil base and the anvil top, wherein the foil interface comprises at least one composite layer ($320_A$, $320_B$, $320_C$) having first and second differing components (313, 315; 323, 325; 333, 335) situated in different corresponding first and second regions in the layer and having a predefined geometric orientation with respect to each other, the first component being a conductive material which provides a predefined resistance to current flow there through so as to generate a desired amount of self-resistive heat in the anvil assembly for a given amount of heating current passing through the first region, and the second component being an electrically insulating material that has sufficient physical strength so as not to be appreciably deformed during each deformation of the specimen.

2. The apparatus in claim 1 wherein each of the first and second regions has the same thickness, but a diameter of the first region differs from that of the second region such that the component in each of the regions exhibits desired physical, electrical and thermal properties.

3. The apparatus in claim 2 wherein the foil interface further comprises multiple, separate ones of the composite layer so as to define a plurality of composite layers arranged in an anvil stack (300).

4. The apparatus in claim 3 wherein each of the composite layers has a predetermined thickness such that resistance provided by all the composite layers, through their corresponding first components, is sufficient to produce the desired amount of said heat in the anvil assembly for the given amount of heating current.

5. The apparatus in claim 4 wherein a conductive disk (317, 327) is situated between successive ones of the composite layers in the stack.

6. The apparatus in claim 5 wherein the conductive disk comprises a tantalum disk.

7. The apparatus in claim 5 wherein the first (or second) component is mica and the second (or first) component is graphite.

8. The apparatus in claim 5 further comprising an insulating holder situated circumferentially around all sides of the anvil stack so as to substantially prevent the heat and the heating current from flowing out the sides of the anvil stack.

9. The apparatus in claim 8 wherein the anvil stack is substantially conical in shape.

10. The apparatus in claim 1 wherein the orientation is substantially concentric, with the first region forming a solid centrally-located disk in the composite layer and having a predefined thickness and diameter, the second region having a ring shape with the same thickness as the first region, wherein the second region is located peripherally around the first region so as to yield a solid disk for the composite layer.

11. The apparatus in claim 10 wherein the foil interface further comprises multiple, separate ones of the composite layer so as to define a plurality of composite layers arranged in an anvil stack (300).

12. The apparatus in claim 11 wherein each of the composite layers has a predetermined thickness such that resistance provided by all the composite layers, through their corresponding first components, is sufficient to produce the desired amount of said heat in the anvil assembly for the given amount of heating current.

13. The apparatus in claim 12 wherein a conductive disk is situated between successive ones of the composite layers in the stack.

14. The apparatus in claim 13 wherein the conductive disk comprises a tantalum disk.

15. The apparatus in claim 13 wherein the first (or second) component is mica and the second (or first) component is graphite.

16. The apparatus in claim 13 further comprising an insulating holder situated circumferentially around all sides of the anvil stack so as to substantially prevent the heat and the heating current from flowing out the sides of the anvil stack.

17. The apparatus in claim 16 wherein the anvil stack is substantially conical in shape.

18. The apparatus in claim 1 wherein the first region contains at least one predefined space for the second region, wherein the space has a circular, triangular or rectilinear shape.

19. The apparatus in claim 18 wherein the foil interface further comprises multiple, separate ones of the composite layer so as to define a plurality of composite layers arranged in an anvil stack.

20. The apparatus in claim 19 wherein each of the composite layers has a predetermined thickness such that resistance provided by all the composite layers, through their corresponding first components, is sufficient to produce the desired amount of said heat in the anvil assembly for the given amount of heating current.

21. The apparatus in claim 20 wherein a conductive disk is situated between successive ones of the composite layers in the stack.

22. The apparatus in claim 21 wherein the conductive disk comprises a tantalum disk.

23. The apparatus in claim 21 wherein the first (or second) component is mica and the second (or first) component is graphite.

24. The apparatus in claim 21 further comprising an insulating holder situated circumferentially around all sides of the anvil stack so as to substantially prevent the heat and the heating current from flowing out the sides of the anvil stack.

25. The apparatus in claim 24 wherein the anvil stack is substantially conical in shape.

* * * * *